United States Patent [19]

Quelet

[11] 4,073,908
[45] Feb. 14, 1978

[54] 8-AMINO-THEOPHYLLINE DERIVATIVES AND APPLICATIONS THEREOF

[75] Inventor: Jean Raymond Quelet, Paris, France

[73] Assignee: Laboratoire le Brun S.A., Paris, France

[21] Appl. No.: 665,567

[22] Filed: Mar. 10, 1976

[30] Foreign Application Priority Data

Mar. 12, 1975 France .............................. 75 07675

[51] Int. Cl.² .................... A61K 31/52; C07D 473/08
[52] U.S. Cl. ................................ 424/253; 260/252; 260/254; 260/256
[58] Field of Search .............. 260/252, 256, 254; 424/253

[56] References Cited

U.S. PATENT DOCUMENTS

| 3,457,263 | 7/1969 | Regnier ............................. 260/252 |
| 3,459,753 | 8/1969 | Boltze et al. ......................... 424/253 |

OTHER PUBLICATIONS

Kochergin et al., "Chem. Abst.", vol. 74, 1971. Abst. No. 125638y.
Kubota et al., Chem. Abst., vol. 71, 59503k (1969).
Kleine et al., C. A., vol. 74, 141704x (1971).

*Primary Examiner*—Alton D. Rollins
*Assistant Examiner*—D. B. Springer
*Attorney, Agent, or Firm*—Young & Thompson

[57] ABSTRACT

This invention relates to 8-amino-theophylline derivatives having the formula:

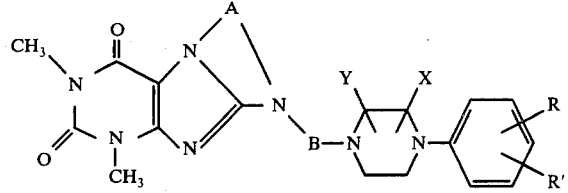

in which A is a straight- or branched-chain lower alkylene radical; B is a straight- or branched-chain lower alkylene radical; X and Y, which may be the same or different, are each hydrogen, lower alkyl or phenoxy alkylene; R represents a halogen atom, an alkyl group having 1-6 carbon atoms, an alkoxy group having 1-6 carbon atoms or a trifluoromethyl group; R' represents a hydrogen atom, a halogen atom, an alkyl group having 1-6 carbon atoms, an alkoxy group having 1-6 carbon atoms or a trifluoromethyl group, and their acid addition salts with inorganic or organic acids.

Said new derivatives have a psychotropic activity.

6 Claims, No Drawings

8-AMINO-THEOPHYLLINE DERIVATIVES AND APPLICATIONS THEREOF

This invention relates to 8-amino-theophylline derivatives and to their therapeutic applications.

The new compounds of this invention have the following general formula:

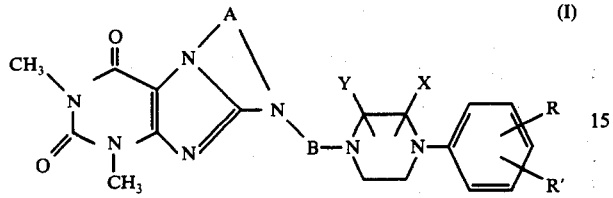
(I)

in which A is a straight- or branched-chain alkylene radical having 2-4 carbon atoms in the straight portion; B is a straight- or branched-chain alkylene radical having 2-6 carbon atoms in the straight portion; X and Y, which may be the same or different, represent each a hydrogen atom, an alkyl group having 1-6 carbon atoms or a phenoxy alkylene group having 1-6 carbon atoms in the alkylene moiety; R represents a halogen atom, an alkyl group having 1-6 carbon atoms, an alkoxy group having 1-6 carbon atoms or a trifluoromethyl group; and R' represents a hydrogen atom, a halogen atom, an alkyl group having 1-6 carbon atoms, an alkoxy group having 1-6 carbon atoms or a trifluoromethyl group.

The invention includes also within its scope the acid addition salts of the compounds of the formula (I) with inorganic or organic acids.

A process for the preparation of compounds of the formula (I), comprises condensing a substituted piperazine having the formula:

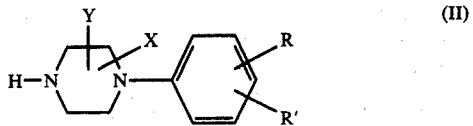
(II)

in which X, Y, R and R' have the above-defined meanings, with a derivative having the formula:

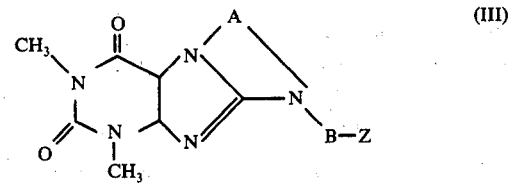
(III)

in which A and B have the above-defined meanings and Z is a halogen atom.

The condensation reaction is generally effected by melting both reagents together.

The derivatives of the formula (III) are prepared by condensing an amino-alcohol with a 7-(haloalkyl)-8-halotheophylline [(M. ECKSTEIN), Dissertationes Pharm., 14, 435-41 (1962)] followed by halogenation of the hydroxyl chain, according to the reaction:

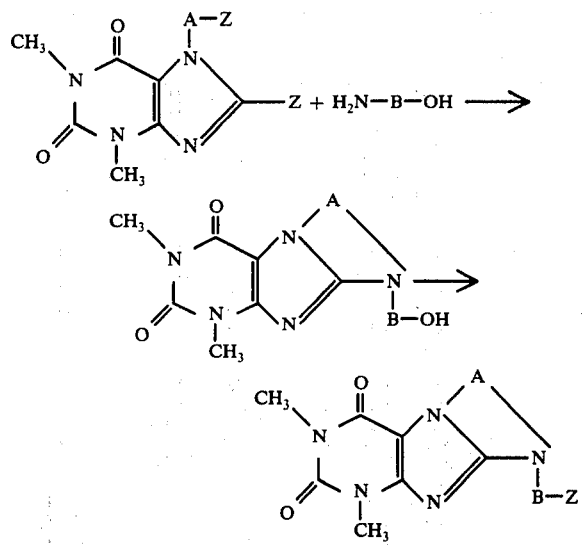

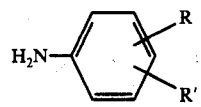

The substituted piperazines of the formula (II) used as starting materials are obtained typically by condensing bis-(β-hydroxyalkyl)amines with substituted anilines of the formula:

$$H_2N-\text{C}_6H_3(R)(R')$$

in hydrochloric acid medium.

The following non limiting Example is given to illustrate the preparation of the compounds of this invention.

EXAMPLE a. Preparation of the halogenated derivative of the formula (III)

A mixture of 9-(β-hydroxyethyl)-1,3-dimethyl-6,7,8,9-tetrahydropyrimidino(2,1-f)purine-2,4(1H,3H)-dione (7g) and thionyl chloride (25 ml) is left aside overnight. The excess thionyl chloride is evaporated off and the resulting material is hydrolyzed in 5N sodium hydroxide (200 ml). The material is then extracted with chloroform, washed with water and dried over sodium sulfate, after which the solvent is evaporated off, to give 5,3 g of chlorinated derivative. M.p. (inst.)= 212° C.

b. Preparation of the derivative of the formula (I)

5.75 g of the chlorinated derivative obtained in a) is condensed with 7.5 g m-chlorophenylpiperazine, by fusing at 180°-190° C during 2 hours. When the condensation is complete, water (50 ml) is added and the resulting material is heated at the boiling temperature, during 15 minutes. The resulting precipitate is filtered, washed with water and recrystallized from ethanol, to give 4.7 g 9-(2-[4-(m-chlorophenyl)piperazin-1-yl]-ethyl)1,3-dimethyl-6,7,8,9-tetrahydropyrimidino(2,1-f)-purine-2,4-dione. M.p. (inst.)= 184° C.

The following Table describes, as Examples, a number of compounds of the formula (I) prepared according to the general procedure of the above example, together with their physical characteristics.

Table I

| Compound No. | A | B | X | Y | R | R' | M.P. °C | U.V. Spectrum max;nm ($\epsilon$) |
|---|---|---|---|---|---|---|---|---|
| 1 | $CH_2$—$CH_2$ | $CH_2$—$CH_2$ | H | H | 3-$CH_3$ | H | 211° | 250(1.30×10⁴);300(1.51×10⁴) |
| 2 | $CH_2$—$CH_2$ | $CH_2$—$CH_2$ | H | H | 3-$CH_3$ | 4-$CH_3$ | 192° | 246(1.66×10⁴);300(1.75×10⁴) |
| 3 | $CH_2$—$CH_2$ | $CH_2$—$CH_2$ | H | H | 3-$OCH_3$ | H | 204° | 249(1.38×10⁴);300(1.51×10⁴) |
| 4 | $CH_2$—$CH_2$ | $CH_2$—$CH_2$ | H | H | 4-$OCH_3$ | H | 177° | 244(1.75×10⁴);301(1.70×10⁴) |
| 5 | $CH_2$—$CH_2$ | $CH_2$—$CH_2$ | H | H | 3-$CF_3$ | H | 198° | 254(1.86×10⁴);302(1.89×10⁴) |
| 6 | $CH_2$—$CH_2$ | $CH_2$—$CH_2$ | H | H | 3-F | H | 181° | 253(2.25×10⁴);300(1.68×10⁴) |
| 7 | $CH_2$—$CH_2$ | $CH_2$—$CH_2$ | H | H | 4-F | H | 249° | 240(1.28×10⁴);299(1.48×10⁴) |
| 8 | $CH_2$—$CH_2$ | $CH_2$—$CH_2$ | H | H | 3-Br | H | 211° | 253(1.53×10⁴);302(1.60×10⁴) |
| 9 | $CH_2$—$CH_2$ | $CH_2$—$CH_2$ | H | H | 3-I | H | 206° | 255(1.58×10⁴);301(1.65×10⁴) |
| 10 | $CH_2$—$CH_2$ | $CH_2$—$CH_2$ | H | H | 2-Cl | H | 192° | 252(1.19×10⁴);298(1.49×10⁴) |
| 11+ | $CH_2$—$CH_2$ | $CH_2$—$CH_2$ | H | H | 3-Cl | H | 29° | 252(1.60×10⁴);298(1.46×10⁴) |
| 12 | $CH_2$—$CH_2$ | $CH_2$—$CH_2$ | H | H | 4-Cl | H | 202° | 247(1.19×10⁴);300(1.50×10⁴) |
| 13 | $CH_2$—$CH_2$ | $CH_2$—$CH_2$ | H | H | 2-Cl | 3-Cl | 217° | 257(1.46×10⁴);301(1.48×10⁴) |
| 14 | $CH_2$—$CH_2$ | $CH_2$—$CH_2$ | H | H | 3-Cl | 4-Cl | 218° | 257(1.49×10⁴);264(1.53×10⁴) 302(1.49×10⁴) |
| 15 | $CH_2$—$CH_2$ | $CH_2$—$CH_2$ | H | H | 3-Cl | 5-Cl | 199° | 264(1.70×10⁴);301(1.63×10⁴) |
| 16 | $CH_2$—$CH_2$ | $CH_2$—$CH(CH_3)$ | H | H | 3-Cl | H | 173° | 254(1.75×10⁴);300(1.68×10⁴) |
| 17 | $CH_2$—$CH_2$ | $CH_2$—$CH_2$—$CH_2$ | H | H | 3-Cl | H | 142° | 2654(1.72×10⁴);300(1.72×10⁴) |
| 18 | $CH_2$—$CH_2$ | $CH_2$—$CH_2$ | H | H | 3-Cl | H | 184° | 256(1.34×10⁴);300(2.11×10⁴) |
| 19 | $CH_2$—$CH_2$—$CH_2$ | $CH_2$—$CH(CH_3)$ | H | H | 3-Cl | H | 196° | 255(1.54×10⁴);301(2.03×10⁴) |
| 20 | $CH_2$—$CH_2$—$CH_2$ | $CH_2$—$CH_2$—$CH_2$ | H | H | 3-Cl | H | 203° | 256(1.35×10⁴);300(2.13×10⁴) |
| 21 | $CH_2$—$CH_2$ | $CH_2$—$CH_2$ | 3-$CH_3$ | H | 3-Cl | H | 176° | 258(1.82×10⁴);302(1.75×10⁴) |
| 22 | $CH_2$—$CH_2$ | $CH_2$—$CH_2$ | 3-$CH_3$ | H | 4-Cl | H | 164° | 248(1.86×10⁴);302(1.61×10⁴) |
| 23 | $CH_2$—$CH_2$ | $CH_2$—$CH_2$ | 3-$CH_3$ | 4-$CH_3$ | 3-Cl | H | 164° | 256(1.47×10⁴);302(1.56×10⁴) |
| 24 | $CH_2$—$CH_2$ | $CH_2$—$CH_2$ | 3-Et | H | 3-Cl | H | 149° | 257(1.85×10⁴);300(1.79×10⁴) |
| 25 | $CH_2$—$CH_2$ | $CH_2$—$CH_2$ | 3-$CH_2$—O$\phi$ | H | 3-Cl | H | 113° | 254(2.25×10⁴);302(1.42×10⁴) |
| 26 | $CH_2$—$CH_2$—$CH_2$—$CH_2$ | $CH_2$—$CH_2$ | H | H | 3-Cl | H | 171° | 254(1.48×10⁴);300(1.96×10⁴) |
| 27 | $CH_2$—$CH_2$—$CH_2$—$CH_2$ | $CH_2$—$CH_2$—$CH_2$ | H | H | 3-Cl | H | 116° | 254(1.70×10⁴);300(2.13×10⁴) |
| 28 | $CH_2$—$CH_2$—$CH_2$ | $CH_2$—$CH_2$—$CH_2$ | H | H | 4-Cl | H | 203° | 254(1.86×10⁴);301(2.08×10⁴) |
| 29 | $CH_2$—$CH_2$ | $(CH_2)_6$ | H | H | 3-Cl | H | 182° | 255(1.57×10⁴);300(1.54×10⁴) |
| 30 | $CH_2$—$CH_2$—$CH_2$ | $(CH_2)_6$ | H | H | 3-Cl | H | 156° | 254(1.48×10⁴);300(2.00×10⁴) |
| 31 | $CH_2CH_2$ | $CH_2$—$CH_2$ | H | H | 3-Cl | H | 255° | 254(1.74×10⁴);298(1.36×10⁴) |

+as the hydrochloride

This invention includes also within its scope a therapeutic composition having, in particular, a psychotropic and anti-inflammatory activity, comprising as active ingredient a compound of the aforementioned formula (I) or a therapeutically acceptable acid addition salt thereof.

The results of a toxicological and pharmacological investigation carried out with the compounds of the formula (I) are set forth below.

A - Toxicological investigation

Acute toxicity in mice by the sub-cutaneous and oral routes and in rats by the oral route was investigated by determination of the death rate following a single administration of increasing dosages.

TABLE II

| Compound No. | ACUTE TOXICITY MICE $LD_{50}$ mg/kg | | RATS |
|---|---|---|---|
| | s.c. route | oral route | oral route |
| 1 | >300 | >300 | >100 |
| 2 | >300 | >300 | >100 |
| 3 | >300 | >300 | >100 |
| 4 | >300 | >300 | >100 |
| 5 | >300 | >300 | >100 |
| 6 | >300 | >300 | >100 |
| 7 | >300 | >300 | >100 |
| 8 | >300 | >300 | >100 |
| 9 | >300 | >300 | >100 |
| 10 | >300 | >300 | >100 |
| 11 | >300 | 450 | 1000 |
| 12 | >300 | 120 | >100 |
| 13 | >300 | >300 | >100 |
| 14 | >300 | >300 | >100 |
| 15 | >300 | >300 | >100 |
| 16 | >300 | >300 | >100 |
| 17 | >300 | >300 | >100 |
| 18 | >300 | >300 | >100 |
| 19 | >300 | >300 | >100 |
| 20 | >300 | >300 | >100 |
| 21 | >300 | >300 | >100 |
| 22 | >300 | >300 | >100 |
| 23 | >300 | >300 | >100 |
| 24 | >300 | 300 | >100 |
| 25 | >300 | >300 | >100 |
| 26 | >300 | >300 | >100 |
| 27 | >300 | >300 | >100 |

TABLE II-continued

| Compound No. | ACUTE TOXICITY MICE $LD_{50}$ mg/kg | | RATS |
|---|---|---|---|
| | s.c. route | oral route | oral route |
| 28 | >300 | >300 | >100 |
| 29 | >300 | >300 | >100 |
| 30 | >300 | >300 | >100 |
| 31 | >300 | 150 | >100 |

Symbol > means that the $LD_{50}$ is not attained at the dosage indicated.

Oral subacute toxicity in rats was investigated by determination of the death rate (if any), of the change in the weight of some organs, and by hematologic examinations, and the like.

Subacute toxicity in 1 month old rats, with compounds Nos. 11 and 18

No fatal issue was noted and the change in weight was normal up to a daily dosage of 100 mg/kg. Similar results were obtained with the other parameters investigated: examination of the blood (red cells, leukocytes, differential leukocyte count, hemoglobin, coagulation time), and weight of some organs (liver, kidneys, spleen, surrenal gland, gonads).

B - Pharmacological investigation

The psychotropic and anti-inflammatory effects of the derivatives of this invention were investigated according to several methods described hereinafter.

1. Motor-stimulant or -depressant activities

The motor-stimulant or -depressant activities were investigated in mice by the sub-cutaneous or oral routes by means of an activometric technique (light-beam activometer).

The dosages which increase or decrease the number of cases over the 50% limit were determined with respect to concomitantly effected reference tests.

Investigation of such activities demonstrated the sedative action of the compounds of this invention, particularly in the case of compound No. 18 which exhibits an $AD_{50}$ of 7.5 mg/kg.

2. Anti-aggressive activities

Were determined:
a. aggressiveness subsequent to electric shocks in mice and rats,
b. aggressiveness subsequent to apomorphine injection (1 mg/kg, in vivo) in rats,
c. aggressiveness subsequent to extended isolation, in mice,
d. aggressiveness in mice-killing rats.

In all cases, the $AD_{50}$ values were determined by the oral route.

All the compounds tested exhibit an anti-aggressive activity, particularly compounds Nos. 11, 3 and 18. The results obtained with the tests effected with these compounds are given in following Table III.

TABLE III

|  | Oral $AD_{50}$ mg/kg | | |
|---|---|---|---|
|  | No. 11 | No. 3 | No. 18 |
| Electric shock in mice | 30 | 30 | 15 |
| Electric shock in rats | 45 | 100 | 45 |
| Apomorphine, in rats | 140 | 180 | 85 |
| Mice-killing rats | 50 | — | 22 |
| Isolated mice | 10 | 25 | 9 |

3. Anti-inflammatory activity

The technique used was that of the carrage eninduced edema in rats (oral route). The dosage which inhibits this edema by a factor of 50% was evaluated by interpolation.

Compounds Nos. 12 and 20 were found to be the more active, the activities being substantially equivalent to those of phenyl butazone.

4. Antalgic activity

The following tests were carried out:
a. writhing test in mice, by the oral route (on intraperitoneal administration of acetic acid),
b. hot-plate test: licking reflex in mice on a plate heated at 65° C.

The compounds exhibit an antalgic activity, the more active being compound No. 18 which exhibits an $AD_{50}$ of 13 mg/kg on administration of acetic acid and of 8.5 mg/kg in the hot-plate test (licking reflex).

5. Anti-histaminic activity

This activity was determined according to the technique of the bronchospasm induced by histamine injection in guinea-pigs.

Among the compounds of this invention, the more active compound is compound No. 12 which exhibits an oral $AD_{50}$ of 1.5 mg/kg.

6. Anti-tussive activity against cough induced by electric stimulation of the laryngeal nerve in cats.

Compound No. 12 is the most active compound investigated.

The following effects of the compounds of this invention were also investigated:
a. Incapacitating effect: rotarod test in mice.
b. Anti-reserpine effect on temperature and ptosis.
c. Anti-convulsant effect with respect to cardiazol in mice.
d. Effect on narcosis induced by pentobarbital and ethanol in mice.
e. Effect on stereotypy induced by apomorphine injection in rats.
f. Effect on learning in rats: Shuttle-box test.

It should be noted that compound No. 11, which exhibits activities which, in most cases, are superior to those of chlordiazepoxide in the anti-aggressive tests does not, as the latter compound, exhibit incapacitating, anti-convulsant, pentobarbital or ethanol-induced narcosis-potentiating, or learning-delaying effects. Superior to Imipramine in the mice-killing test in rats, it is to be distinguished from this material by its absence of anti-reserpinic effect. It is also free from typical neuroleptic effects: absence of apomorphinic anti-stereotypy, of catalepsy and of ptosis.

Compound No. 18, which has the same characteristics, is, however, more sedative and more antalgic and potentiates ethanol-induced narcosis. Another noteworthyl difference, with respect to compound No. 11, is its antagonistic activity on the group toxicity of amphetamine in mice ($AD_{50}$ 20 mg/kg).

It is apparent from the results of the above investigations that the compounds of this invention possess a psychotropic activity and an anti-inflammatory activity.

The therapeutic composition of this invention may be formulated, for oral administration, as tablets, drops, drinkable solutions. It may also be formulated for rectal and parenteral administration according to the suitable conventional techniques.

Each unit dose may advantageously contain from 1 mg to 100 mg active ingredient.

In view of its psychotropic activity, the therapeutic composition of this invention is applicable to the treatment of psychoses and neuroses.

Having now described my invention what I claim as new and desire to secure by Letters Patent is:

1. A compound selected from the group consisting of the 8-amino-theophylline derivatives having the formula:

in which A is a member selected from the group consisting of straight- and branched-chain alkylene radicals having 2–4 carbon atoms in the alkylene portion; B is a member selected from the group consisting of straight- and branched-chain alkylene radicals having 2–6 carbon atoms in the alkylene portion; X and Y are members individually selected from the group consisting of hydrogen, straight-chain alkyl having 1–6 carbon atoms and phenoxy-alkylene having 1–6 carbon atoms in the alkylene moiety; R is a member selected from the group consisting of halogen, straight-chain alkyl having 1–6 carbon atoms, alkoxy having 1–6 carbon atoms and trifluoromethyl; and R' is a member selected from the group consisting of hydrogen, halogen, straight-chain alkyl having 1–6 carbon atoms, alkoxy having 1–6 carbon atoms and trifluoromethyl; and their therapeutically acceptable acid addition salts.

2. 8-(2-[4-(m-Methoxyphenyl)-piperazin-1-yl]-ethyl)1,3-dimethyl-6,7-dihydro-8-H-imidazo[2,1-f]purine-2,4(1H,3H)dione or its therapeutically acceptable acid addition salts.

3. 8-(2-[4-(m-Chlorophenyl)piperazin-1-yl]-ethyl)1,3-dimethyl-6,7-dihydro-8-H-imidazo[2,1-f]purine-2,4(1H,3H)dione, or its therapeutically acceptable acid addition salts.

4. 9-(2-[4-(m-Chlorophenyl)-piperazin-1-yl]-ethyl) 1,3-dimethyl-6,7,8,9-tetrahydropyrimidino[2,1-f]purine-2,4(1H,3H)-dione, or its therapeutically acceptable acid addition salts.

5. A therapeutic composition having a sedative and anti-aggressive psychotropic activity consisting essentially of a therapeutically effective amount of a compound selected from the group consisting of 8-aminotheophylline derivatives having the formula:

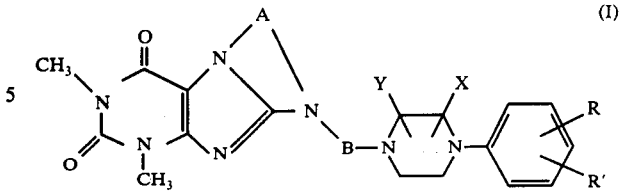

in which A is a member selected from the group consisting of straight- and branched-chain alkylene radicals having 2–4 carbon atoms in the alkylene portion; B is a member selected from the group consisting of straight- and branched-chain alkylene radicals having 2–6 carbon atoms in the alkylene portion; X and Y are members individually selected from the group consisting of hydrogen, straight-chain alkyl having 1–6 carbon atoms and phenoxy-alkylene having 1–6 carbon atoms in the alkylene moiety; R is a member selected from the group consisting of halogen, straight-chain alkyl having 1–6 carbon atoms, alkoxy having 1–6 carbon atoms and trifluoromethyl; and R' is a member selected from the group consisting of hydrogen, halogen, straight-chain alkyl having 1–6 carbon atoms, alkoxy having 1–6 carbon atoms and trifluoromethyl; and their therapeutically acceptable acid addition salts, together with a therapeutically acceptable vehicle.

6. A therapeutic composition as claimed in claim 5, in unit dosage form, each unit dose containing 1–100 mg active ingredient.

* * * * *